United States Patent [19]

Takeda et al.

[11] Patent Number: 4,886,817
[45] Date of Patent: Dec. 12, 1989

[54] IMIDAZOLIDINONES AS BRAIN ACTIVATORS

[75] Inventors: Mikio Takeda, Urawa; Masaru Inage, Kitamoto; Hiroshi Wada, Nishinomiya; Hajime Tamaki, Sakado; Takashi Ochiai, Kobe, all of Japan

[73] Assignee: Tanabe Seiyaku Co., Ltd., Japan

[21] Appl. No.: 292,211

[22] Filed: Dec. 29, 1988

Related U.S. Application Data

[63] Continuation-in-part of Ser. No. 115,719, Nov. 2, 1987, abandoned.

[30] Foreign Application Priority Data

Nov. 14, 1986 [JP] Japan ................... 61-272655

[51] Int. Cl.[4] ..................... A61K 31/44; C07D 401/04
[52] U.S. Cl. .................... 514/341; 514/252; 514/256; 514/269; 514/273; 514/274; 514/275; 514/365; 514/369; 514/371; 544/238; 544/298; 544/316; 544/317; 544/321; 544/322; 544/327; 544/329; 544/332; 544/335; 544/336; 544/408; 544/409
[58] Field of Search ............... 514/252, 256, 269, 273, 514/274, 275, 341, 365, 369, 371; 544/238, 298, 316, 317, 321, 322, 327, 329, 332, 335, 336, 408, 409; 546/278; 548/185, 187, 196, 204

[56] References Cited

U.S. PATENT DOCUMENTS 4,600,430  7/1986  Abdulla et al. ..................... 71/92

FOREIGN PATENT DOCUMENTS 61-33172   2/1986  Japan ..................... 546/278
61-194082  8/1986  Japan ..................... 546/278

OTHER PUBLICATIONS

*Chemical Abstracts*, 104:207273c (1986).

Primary Examiner—Richard A. Schwartz
Attorney, Agent, or Firm—Scully, Scott, Murphy & Presser

[57] ABSTRACT

This invention relates to imidazolidinone compounds of the formula

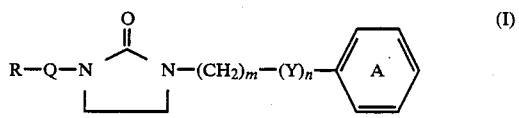

wherein
Q is methylene group or a single bond:
R is a heterocyclic group selected from the group consisting of pyridyl, pyridazinyl, pyrimidinyl, pyrazinyl and 1,3-thiazolyl which may be unsubstituted or with a substituent selected from the group consisting of lower alkyl, lower alkoxy and halogen atom, wherein R is bonded to Q or, when Q is a single bond, to the imidazolidinone ring, through the carbon atom of R;
the ring A is an unsubstituted phenyl or a substituted phenyl having 1 or 2 substituent(s) selected from the group consisting of lower alkyl, lower alkoxy, halogen, lower alkylthio, trihalogeno-lower alkyl and nitro;
Y is vinylene group or ethynylene;
m is a integer from 1 to 6 and
n is 0, 1 or 2, or a pharmacetically acceptable salt thereof.
These compounds aer useful as cerebral activators, anti-depressants and nootropic drugs.

16 Claims, No Drawings

IMIDAZOLIDINONES AS BRAIN ACTIVATORS

REFERENCE TO RELATED APPLICATION

The instant application is a continuation-in-part of U.S. patent application Ser. No. 115,719, filed November 2, 1987, now abandoned.

BACKGROUND OF THE INVENTION

This invention relates to a novel imidazolidinone compound and processes for preparing the same.

1-pyrrolidinoethyl-3-pyridyl-2-imidazolidinone compounds are known to exhibit gastric motion promoting action, while 1-alkyl-3-pyridyl-2-imidazolidinone compounds exhibit herbicidal activity (See Japanese Unexamined Patent Publications Nos. 33172/1986).

SUMMARY OF THE INVENTION

This invention relates to a novel imidazolidinone compound of the following formula

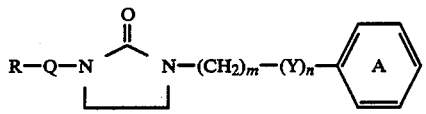

wherein Q is a methylene group or a single bond;

R is a heterocyclic group selected from the group consisting of pyridyl, pyridazinyl, pyrimidinyl, pyrazinyl, and 1,3-thiazolzyl, which may be unsubstituted or substituted by a substituent selected from the group consisting of lower alkyl, lower alkoxy and halogen, and wherein R is bonded to Q or, when Q is a single bond, to the imidazolidinone ring, through the carbon atom of R;

the ring A is an unsubstituted phenyl group or a phenyl group having 1 or 2 substituents selected from the group consisting of lower alkyl, lower alkoxy, halogen, lower alkylthio, trihalogeno-lower alkyl and nitro;

Y is vinylene or ethynylene;

m is an integer from 1 to 6 and n is 0, 1 or 2 or a pharmaceutically acceptable salt thereof.

DESCRIPTION OF THE PREFERRED EMBODIMENTS

The imadazolidinone compounds (I) and their salts show potent activating effect on cerebral metabolism, nootropic effect and/or antidepressive effect, and are useful as brain activators.

As used herein, the lower alkyl groups either singly or in combination with other groups contain up to 4 carbon atoms which may be in the normal or branched configuration including but not limited to methyl, ethyl, propyl, isoprpyl, butyl, isobutyl, t-butyl and the like.

Halogen, as defined herein is chlorine, fluorine, bromine and iodine.

The preferred values of R in Formula I are pyridyl, lower alkyl-pyridyl or pyrimidinyl. Especially preferred values of R include pyridyl, methylpyridyl and pyrimidinyl group. The most preferred value of R is 3-pyridyl, 4-pyridyl, 6-methyl-2-pyridyl or 2-pyrimidinyl.

The preferred values of ring A is unsubstituted phenyl or a phenyl group having a substituent selected from the group consisting of lower alkyl, lower alkoxy, halogen and trihalogenomethyl. More specifically, the preferred values of ring A include unsubstituted phenyl, methylphenyl, methoxyphenyl, chlorophenyl or trifluoromethylphenyl. Especially preferred values of ring A are unsubstituted phenyl, 2-methylphenyl, 3-methylphenyl, 2-methoxyphenyl, 3-methoxyphenyl, 2-chlorophenyl, 3-clorophenyl, 4-chlorophenyl, 2-trifluoromethylphenyl or 3-trifluoromethylphenyl. The most preferred values of ring A include unsubstituted phenyl, 3-methylphenyl, 2-chlorophenyl, 3-chlorophenyl and 4-chlorophenyl.

It is preferred that Q is a single bond.

The preferred value of Y is vinylene.

Preferred values of m are 1,2, or 3. Especially preferred values of m are 1 and 3.

The preferred value of n is 1.

It is preferred that Y is vinylene when R is pyridyl or substituted pyridyl wherein the substituents are lower alkyl, lower alkoxy or halogen; pyridazinyl; pyrimidinyl; pyrazinyl; or 3-thiazolyl. More specifically, it is preferred that when R is pyridyl or lower alkyl pyridyl or pyrimidinyl group, Y is vinylene.

Examples of the imidzolidinone compound (I) of the present invention include those wherein, in the formula (I), R is a heterocyclic group such as pyridyl group, pyridazinyl group, pyrimidinyl group, pyrazinyl group or 1,3-thiazolyl group (said heterocyclic group may optionally have a substituent selected from a lower alkyl group such as methyl group, ethyl group, propyl group, butyl group, etc., a lower alkoxy group such as methoxy group, ethoxy group, propoxy group, butoxy group, etc., and a halogen atom such as chlorine atom, fluorine atom, bromine atom, iodine atom, etc.); the ring A is phenyl group or a phenyl group having 1 to 2 substituent(s) selected from the group consisting of a lower alkyl group such as methyl group, ethyl group, propyl group, butyl group, etc.; a lower alkoxy group such as methoxy group, ethoxy group, propoxy group, butoxy group, etc.; a halogen atom such as chlorine atom, bromine atom, fluorine atom, iodine atom, etc.; a lower alkylthio group such a methylthio group, ethylthio group, propylthio group, butylthio group, etc.; a trihalogeno-lower alkyl group such as trifluoromethyl group, etc., and nitro group; Y is vinylene group or ethynylene group; m is 1 to 6; n is 0, 1 or 2; and Q is methylene group or a single bond. The preferred examples include those wherein, in formula (I), R is a pyridyl group, or a pyridyl group having a substituent selected from the group consisting of lower alkyl group, a lower alkoxy group and a halogen atom, pyridazinyl group, pyrimidinyl group, pyrazinyl group or 1,3-thiazolyl group; the ring A a is phenyl group or a phenyl group having 1 to 2 substituent(s) selected from the group consisting of a lower alkyl group, a lower alkoxy group, a halogen atom, a lower alkylthio group, a trihalogeno-lower alkyl group and nitro group; Y is vinylene group or ethynylene group; m is 1 to 6; n is 0, 1 or 2; and Q is a methylene group or a single bond. Further preferred examples include those wherein, in the formula (I), R is a pyridyl group, a lower alkoxy-pyridyl group, a lower alkyl pyridyl group, a pyridazinyl group or a pyrimidinyl group; the ring A is A phenyl group or a phenyl group having 1 to 2 substituent(s) selected from the group consisting of a lower alkyl group, a lower alkoxy group, a halogen atom, a lower alkylthio group, a trihalogeno-lower alkyl group and nitro group; Y is a vinylene group; m is 1 to 6; n is 0, 1 or 2; and Q is a methylene group or a single bond. Other preferred examples include those wherein, in the formula (I), R is a pyridyl group, a methylpyridyl group, or pyrimidinyl group; the ring A is a phenyl group or a phenyl group having a substituent selected from the group consisting of a lower alkyl group, a lower alkoxy group, a halogen atom and a trihalogeno-methyl group; Y is vinylene group; m is 1 to 4; n is 0, 1 or 2; and Q is a single bond. In this embodiment, it is preferred that ring A is a phenyl, or a methylphenyl group, a methoxyphenyl group, chlorophenyl group or a trifluoromethylphenyl group. Still other preferred examples includes those wherein, in the formula (I), R is a pyridyl group, a methyl pyridyl group, or a pyrimidinyl group; the ring A is a phenyl group, a methylphenyl group or chlorophenyl group; Y is vinylene group; m is 1 to 3; n is 1; and Q is a single bond. The most preferred examples include those wherein, in the formula (I), R is 3-pyridyl, 4-pyridyl, 6-methyl-2-pyridyl or 2-pyrimidinyl; the ring A is a phenyl, a 2-methylphenyl, 3-methylphenyl, 2-methoxyphenyl, 3-methoxyphenyl, 2-chlorophenyl, 3-chlorophenyl, 4-chlorophenyl, 2-trifluoromethylphenyl or 3-trifluoromethylphenyl; Y is vinylene; m is 1 to 3; n is 1; and Q is a single bond. Moreover in this latter list, it is most especially preferred that the ring A is phenyl, 3-methylphenyl, 2-chlorophenyl, or 3-chlorophenyl group and m is 1 or 3.

The preferred compounds of the present invention include 1-cinnamyl-3-(3-pyridyl)-2-imidazolidinone and 1-cinnamyl-3-(6-methyl-2-pyridyl)-2-imidazolidinone or pharmaceutically acceptable salts thereof. The most preferred examples include (E)-1-cinnamyl-3-(3-pyridyl)-2-imidazolidinone and (E)-1-cinnamyl-3-(6-methyl-2-pyridyl)-2-imidazolidinone or the pharmaceutically acceptable salts thereof.

In the present invention, unless otherwise defined, the vinylene group of the formula: —CH=CH— may exist in either the cis-form (namely (Z)-configuration) and trans-form (namely (E)-configuration) of the formulae:

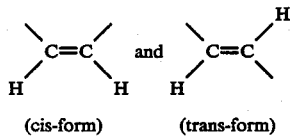

(cis-form)         (trans-form)

or a mixture thereof.

The compound (I) of the present invention can be prepared by, for example, (Process A): condensing a compound (II) of the formula:

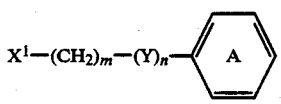

wherein the ring A, Y, m and n have the same meanings as defined above and $X^1$ represents a reactive residue, with a compound (III) of the formula:

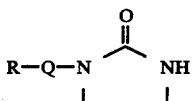

wherein R and Q have the same meanings as defined above, or a salt thereof, or by (Process B): reacting a compound (IV) of the formula:

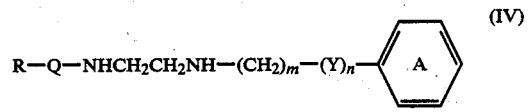

wherein the symbols have the same meanings as defined above, or a salt thereof with a carbonylating agent.

The compound (I) can be also prepared by
(Process C): reacting a compound (V) of the formula:

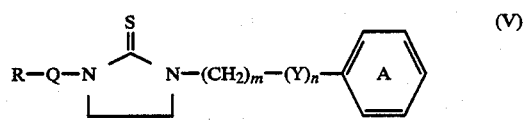

wherein the symbols have the same meanings as defined above, or a salt thereof with an oxidizing agent, or
(Process D): condensing a compound (VI) of the formula:

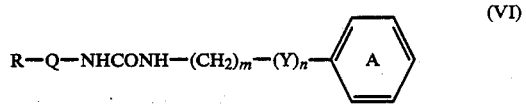

wherein the symbols have the same meanings as defined above, or a salt thereof with a compound (VII) of the formula:

wherein $X^2$ and $X^3$ represent reactive residues.

As the salts of the starting compounds (III), (IV), (V) and (VI), for example, there may be suitably employed any of the mineral acid addition salts such as hydrochloride and sulfate, organic acid addition salts such as oxalate and tartrate, or alkali metal salts as sodium salt and potassium salt.

(Process A) and (Process D)

These reactions can be carried out in the presence or absence of an acid acceptor in an appropriate solvent. Examples of compounds (II) and (VII) may include compounds wherein the reactive residues, $X^1$, $X^2$ and $X^3$ are, for example, halogen atoms (e.g. chlorine atom, bromine atom, iodine atom, etc.), lower alkylsulfonyloxy groups (e.g., methylsulfonyloxy group, ethylsulfonyloxy group, etc.), and substituted or unsubstituted phenylsulfonyloxy groups (e.g., a phenylsulfonyloxy group, a p-toluenesulfonyloxy group, etc.). Suitable examples of the acid acceptor include either inorganic or organic bases such as an alkali metal alkoxide, an alkali metal hydroxide, an alkaline earth metal hydroxide, an alkali metal carbonate, an alkali metal hydrogen carbonate, an alkyl alkali metal, an alkali metal amide, an alkali metal hydride, triethylamine, trimethylamine, N-methylmorpholine, tetrabutylammonium salt, etc. Further, KF-alumina, KF-cerite, KF-silica gel, etc. may be also used for this purpose. As the appropriate solvent, conventional solvents can be widely used, such as acetone, dimethylformamide, dimethyl sulfoxide, tetrahydrofuran, dioxane, chloroform, water or a mixture of these. These reactions can proceed suitably at −70° C. to 100° C., particularly −30° C. to 25° C.

(Process B)

This reaction can be carried out either in the presence or absence of a base in a solvent. As the carbonylating agent, for example, di-lower alkyl carbonate such as diethyl carbonate, phosgene, carbonyl diimodazole, disuccinimide carbonate, etc. can be suitably used. When phosgene is used as the carbonylating agent, it is preferably carried out in the presence of a base, and preferred examples of such bases may include organic amines such as triethylamine, trimethylamine, pyridine, imidazole, and the like. As the solvent, chloroform, tetrahydrofuran, dioxane, benzene, dimethylformamide, etc. may be preferably used. This reaction can proceed preferably at −30° C. to 60° C., particularly −10° C. to 10° C.

(Process C)

The reaction of compound (V) or a salt thereof with the oxidizing agent can be carried out in an appropriate solvent. As the oxidizing agent, nitrous acid or dimethyl sulfoxide-trifluoroacetic acid, etc. can be suitably used. For example, when nitrous acid is used as the oxidizing agent, the reaction can preferably be carried out by dissolving the compound (V) or a salt thereof and a mineral acid (e.g. hydrochloric acid, sulfuric acid (e.g. hydrochloric acid, sulfuric acid, hydrobromic acid, etc.) in a solvent and subsequently adding a solution of an alkali metal nitrite such as of sodium nitrite, potassium nitrite, etc. As the solvent in this case, water, lower alkanols such as methanol, ethanol and the like, dioxane, tetrahydrofuran or mixtures thereof can be suitably used. This reaction can proceed suitably at −20° C. to 50° C., particularly −10° C. to 25° C.

The compound (I) of the present invention and a salt thereof are useful as a cerebral activator. More particularly, Compound (I) and a salt thereof can effectively prolong the survival time of mice suffering from KCN-induced cerebral anoxia or hypobaric hypoxia, and show potent protective action against brain ischemia. Compound (I) and a salt thereof can also improve KCN-induced cerebral energy metabolism disorders. Further, Compound (I) and a salt thereof improve scopolamine-induced amnesia, and show potent anti-convulsive, AChE (acetylchline esterase) inhibitory and GABA-mimetic or GABA-potentiative actions. For example, Compound (I) of the present invention shows not only the protective effects against maximum electroshock-induced convulsion and KCN-induced cerebral anoxia as shown in the following Experiments 1 and 2, but (E)-1-cinnamyl-3-(3-pyridyl)-2-imidazolidinone of the present invention, at a dose of 30 mg/kg (p.o.), can also significantly prolong the survival time of mice which suffered from hypobaric hypoxia by keeping said mice in a closed container under reduced pressure (pressure: 165 mmHg). Moreover, while KCN is known to induce various disorders of cerebral energy metabolisms such as the significant decrease in ATP, creatine-P, glucose or glycogen in the brain, (E)-1-cinnamyl-3-(3-pyridyl)-2-imidazolidinone could also inhibit the decrease in such energy metabolism-relating substances and improve the KCN-induced cerebral metabolism disorders. Based on these therapeutic effects, Compound (I) and a salt thereof can be used as a cerebral metabolism activator and/or a nootropic drug.

Compound (I) of the present invention and a salt thereof can also be used as antidepressants because it can effectively shorten the immobility time of mice during forced swimming thereof and also increase spontaneous locomotor activity. For example, (E)-1-cinnamyl-3-(3-pyridyl)-2-imidazolidinone of the invention at a dose of 45 mg/kg showed a significant increase in the spontaneous locomotion in mice which received apomorphine (dose 0.03 or 0.1 mg/kg, s.c.) after oral administration thereof.

In addition, Compound (I) and a salt thereof may have also an inhibitory effect on gastric juice secretion and may be used for therapy and prophylaxy of peptic ulcer. For example, when the amount of gastric juice was measured 5 hours after intraperitoneal administration of a test compound to pylorus ligated rats, (2E,4E)-1-[5-(2-chlorophenyl)-2,4-pentadienyl]-3-(4-pyridyl)-2-imidazolidinone and (E)-1-cinnamyl-3-(3-pyridyl)-2-imidazolidinone hydrochloride of the invention at a dose of 30 mg/kg showed not less that 42% decrease in gastric juice secretion. Further, the compound of the present invention is low in toxicity and has high safety as pharmaceuticals. For example, the acute toxicity ($LD_{50}$) of (E)-1-cinnamyl-3-(3-pyridyl)-2-imidazolidinone which was estimated 7 days after oral administration thereof to male Std/ddY mice was more than 1500 mg/kg.

Compound (I) can be used either as a free base or as a salt thereof. Pharmacologically acceptable salts may include, for example, salts with inorganic acids such as hydrochloric acid, sulfuric acid and hydrobromic acid; salts with organic acids such as oxalic acid, methanesulfonic acid and tartaric acid; addition salts with amino acids such as glycine, lysine, arginine, aspertic acid and glutamic acid, and the like. These salts can be prepared by, for example, treating the free compound (I) with corresponding acids.

Compound (I) or a salt thereof can be administered either orally pr parentally (e.g. intravenously, intramuscularly, intracutaneously). The dose of Compound (I) or a salt thereof may vary depending on the age, body weight, condition of the patient and the kind of severity of diseases, but may be usually about 1 to about 100 mg, preferably 5 to 50 mg per 1 kg of body weight per day. Compound (I) or a salt thereof may be used as a pharmaceutical preparation in association or admixture with a pharmaceutical excipient suitable for oral or parenteral administration. The pharmaceutical preparation may be a solid preparation such as tablet, granule, capsule, or a liquid preparation such as solution, suspension and emulsion. The pharmaceutical preparations are sterilized and/or may also contain auxiliary agents such as stabilizers, wetting agents and emulsifiers.

The starting compound (II) of the present invention can be prepared according to, for example, the method described in Journal of Medicinal Chemistry 8, 326 (1965). Alternatively, it may be prepared by (1)-(a) treating a compound of the formula:

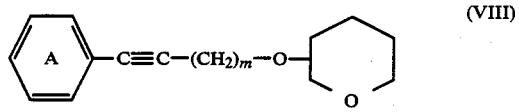

(VIII)

wherein the symbols have the same meanings as defined above, with an acid (e.g. p-tuluenesulfonic acid); or (1)-(b) reducing said compound (VIII) with lithium aluminum hydride, followed by acid treatment; and (2) subsequently converting the hydroxy group of the resultant product of the formula:

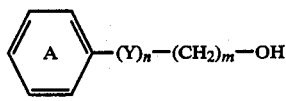 (IX)

wherein the symbols have the same meanings as defined above, to a reactive residue in a conventional manner. Further, the starting compound (II) can be also obtained by converting the hydroxy group of a compound of the formula:

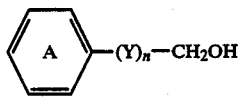 (X)

wherein the symbols have the same meanings as defined above, to a reactive residue in a conventional manner, and subsequently, if desired, applying the malonic ester synthetic method ("Organic Chemistry", by Hammond, 3rd edition, p. 428, published by Hirokawa Shoten) repeatedly. In preparation of the above starting material, the compound (IX) wherein Y is vinylene group and m=3 can be prepared by, for example, reacting a compound of the formula:

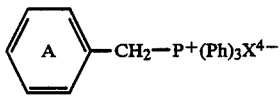

wherein $X^4$ represents a halogen atom, and the ring A has the same meaning as defined above, with 2-hydroxytetrahydrofuran in the presence of a base (e.g. n-butyl lithium) at room temperature.

On the other hand, the starting compound (III) can be prepared according to, for example, the following reaction schemes.

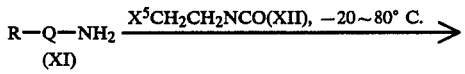

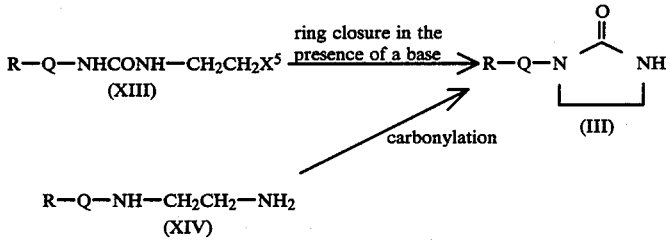

wherein $X^5$ represents a halogen atom, and R and Q have the same meanings as defined above.

The starting compound (IV) can be obtained by reacting the compound (II) with (XIV) under the same conditions as described in (Process A), the starting compound (V) by treating the starting compound (IV) with a thiocarbonylating agent (e.g. diethyl thiocarbonate, thiophosgene, thiocarbonyl diimidazole, disuccinimide thiocarbonate) under the same conditions as described in (Process B), and further the starting compound (VI) by treating the above compound (XI) and an amine compound of the formula:

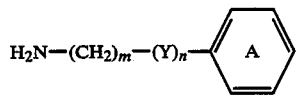

wherein the symbols have the same meanings as defined above, with a carbonylating agent under the same conditions as described in (Process B).

Throughout the specification and claims, the term "lower alkyl" and "lower alkoxy" denote an alkyl having 1 to 4 carbon atoms and an alkoxy having 1 to 4 carbon atoms, respectively.

EXPERIMENT 1

(Preventive effect on maximum electroshock-induced convulsion)

(Method)

One hour after oral administration of a test compound to male Std/ddY mice, maximum electroshock (AC 900 V, 25 mA, 0.15 second) was delivered to said mice through corneal electrodes from an electrical stimulator. The number of mice which showed the protection against the tonic extensive convulsion were counted.

(Results)

The compounds of the present invention listed below completely inhibited the tonic extensive convulsion induced by maximum electroshock at a dose of 100 mg/kg.

| Test compound Nos. | Chemical name |
|---|---|
| 1. | (E)-1-(4-chlorocinnamyl)-3-(3-pyridyl)-2-imidazolidinone |
| 2. | (E)-1-(4-chlorocinnamyl)-3-(4-pyridyl)-2-imidazolidinone |
| 3. | (E)-1-cinnamyl-3-(3-pyridyl)-2-imidazolidinone hydrochloride |
| 4. | (E)-1-cinnamyl-3-(2-pyrimidinyl)-2-imidazolidinone |
| 5. | (E)-1-(3-chlorocinnamyl)-3-(4-pyridyl)-2-imidazolidinone |
| 6. | (E)-1-(2-chlorocinnamyl)-3-(4-pyridyl)-2-imidazolidinone |
| 7. | (E)-1-(3-methylcinnamyl)-3-(4-pyridyl)-2-imidazolidinone |
| 8. | (E)-1-(5-phenyl-4-pentenyl)-3-(4-pyridyl)-2-imidazolidinone |
| 9. | (Z)-1-cinnamyl-3-(4-pyridyl)-2-imidazolidinone |

EXPERIMENT 2

(Preventive effect on KCN induced cerebral anoxia)

(Method)

One hour after oral administration of a test compound to male Std/ddY mice (one group: 5 mice), KCN was intravenously administered (dose: 2.4 mg/kg) to said mice, and then survival time was measured.

(Results)

In this experiment, Compound Nos. 1 to 9 mentioned in Experiment 1 showed excellent prolongation of the survival times of mice suffered from KCN induced cerebral anoxia. Namely, no death was observed in any of the mice tested when Compound Nos. 1 to 9 were administered at a dose of 100 mg/kg respectively. On the other hand, 5 mice of the control group which were not administered the test compound died soon after the injection of KCN.

EXAMPLE 1

(1) To a solution of 150 g of 3-aminopyridine dissolved in 1000 ml of toluene, 176 g of 2-chloroethylisocyanate was added dropwise over 30 minutes under cooling. After stirring at room temperature for 5 hours, the precipitated crystals were collected by filtration to give 318 g of N-(2-chloroethyl)-N'-(3-pyridyl) urea.

M.P. :136°–138° C.

(2) To a mixture of 150 g of N-(2-chloroethyl)-N'-(3-pyridyl) urea dissolved in 500 ml of tetrhydrofuran and 500 ml of dimethylformamide, 31.6 g of sodium hydride (60% oily suspension) was added under ice-cooling over 20 minutes. After stirring under ice-cooling for 10 minutes and at room temperature for 2 hours, 10 ml of acetic acid was added and the solvent was distilled off. Saturated saline water and chloroform were added to thr residue and insolubles were separated by filtration. The chloroform layer was washed with sodium hydrogen carbonate solution, dried and the solvent was distilled off. The residue was recrystallized from a mixture of chloroform and hexane to give 108.5 g of 1-(3-pyridyl)-2-imidazolidinone.

M.P.: 161°–163° C.

(3) To a solution of 150 g of 1-(3-pyridyl)-2-imidazolidinone dissolved in 1500 ml of N,N-dimethylformamide was added 40 g of sodium hydride (60% oily dispersion). After the mixture was stirred at room temperature for 10 minutes, 154 g of cinnamyl chloride (trans-form) was added dropwise under ice-cooling and the mixture was stirred for 2 hours. After addition of 10 ml of acetic acid, the solvent was distilled off under reduced pressure and to the residue was added water, followed by extraction with chloroform. After washing with saturated aqueous sodium hydrogen carbonate and saturated saline water, the extract was dried. Chloroform was distilled off, and isopropyl ester was added to the residue. The precipitated crystals were collected by filtration and recrystallized from ethanol to give 238.1 g of (E)-1-cinnamyl-3-(3-pyridyl)-2-imidazolidinone as colorless prisms.

Yield: 92.7%.

M.P.: 114.5°–116° C.

Hydrochloride (polymorphism):

M.P. 188°–190° C. (recrystallized from methanolisopropanol),

206°–209° C. (recrystallized from methanolisopropanol).

Hydrobromide:

M.P. 180°–199° C. (recrystallized from isopropanol).

Sulfate:

M.P. 195°–198° C. (recrystallized from ethanolmethanol).

Methanesulfonate:

M.P. 155°–156° C. (recrystallized from isopropanol).

EXAMPLES 2 to 41

By treating 1-(3-pyridyl)-2-imidazolidinone obtained in Example 1-(2) and a cinnamyl compound (II) in the same manner as in Example 1-(3), the compounds shown below in Tables 1-1 to 1-4 were obtained.

TABLE 1-1

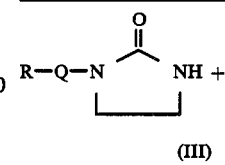

(III)

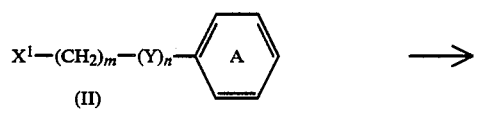

(II)

($X^1$ = chlorine atom or p-toluenesulfonyl group)

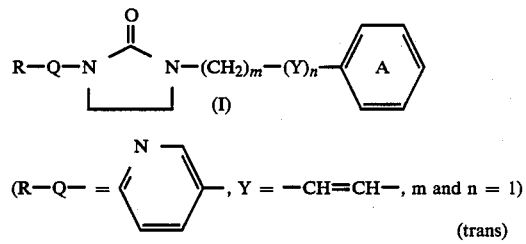

$(R-Q-$ =

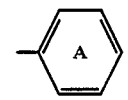

, $Y = -CH=CH-$, m and n = 1)

(trans)

Compound (I)

| Example No. | —A 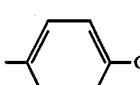 | Yield % | M.P. (Solvent used for recrystallization) |
|---|---|---|---|
| 2 | 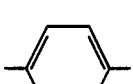—Cl | 75.1 | 137~138° C. (isopropanol) |
| 3 | 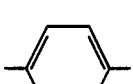—OCH₃ | 59.3 | 138~139.5° C. (isopropanol) |
| 4 | 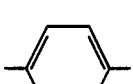—CH₃ | 60.1 | 107.5~109° C. (isopropanol) |
| 5 | —OCH₃ | 60.2 | 75~77° C. (isopropanol-isopropyl ether) |

TABLE 1-1-continued

| No. | Substituent | Yield % | M.P. (Solvent used for recrystallization) |
|---|---|---|---|
| 6 | 4-CH₃-phenyl | 59.7 | 96~98° C. (isopropanol-isopropyl ether) |
| 7 | 2-CH₃-phenyl | 64.3 | 115.5~118° C. (isopropanol) |
| 8 | 4-Cl-phenyl | 65.3 | 117~118.5° C. (isopropanol) |
| 9 | 2-CH₃O-phenyl | 41.0 | 91.5~93° C. (isopropanol-isopropyl ether) |
| 10 | 2-Cl-phenyl | 68.3 | 133.5~135° C. (isopropanol) |
| 11 | 4-F-phenyl | 73.7 | 133~134.5° C. (isopropanol) |
| 12 | 3,4-diCl-phenyl | 61.3 | 137~140° C. (isopropanol) |
| 13 | 2-F-phenyl | 57.6 | 109~110.5° C. (isopropanol) |
| 14 | 3-CF₃-phenyl | 48.9 | 95~100° C. (isopropanol) |
| 15 | 2-CF₃-phenyl | 61.3 | 119.5~121° C. (isopropanol) |
| 16 | 4-CF₃-phenyl | 40.1 | 117.5~119° C. (isopropanol) |
| 17 | 3-NO₂-phenyl | 38.3 | 106~111° C. (chloroform-isopropyl ether) |
| 18 | 4-SCH₃-phenyl | 61.3 | 81.5~83.5° C. (isopropanol-isopropyl ether) |
| 19 | 4-SCH₃-phenyl | 70.0 | 130~131.5° C. (isopropanol) |
| 20 | 3-CH₃S-phenyl | 66.4 | 84.5~87° C. (isopropanol) |
| 21 | 2,3-diCl-phenyl | 72.3 | 96~98.5° C. (isopropyl ether) |
| 22 | 2,4-diCl-phenyl | 60.1 | 105.5~107° C. (diethyl ether) |

TABLE 1-2

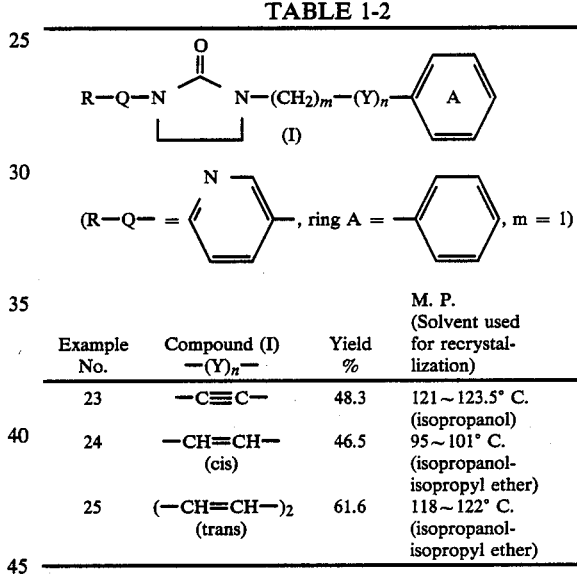

| Example No. | Compound (I) —(Y)ₙ— | Yield % | M.P. (Solvent used for recrystallization) |
|---|---|---|---|
| 23 | —C≡C— | 48.3 | 121~123.5° C. (isopropanol) |
| 24 | —CH=CH— (cis) | 46.5 | 95~101° C. (isopropanol-isopropyl ether) |
| 25 | (—CH=CH—)₂ (trans) | 61.6 | 118~122° C. (isopropanol-isopropyl ether) |

TABLE 1-3

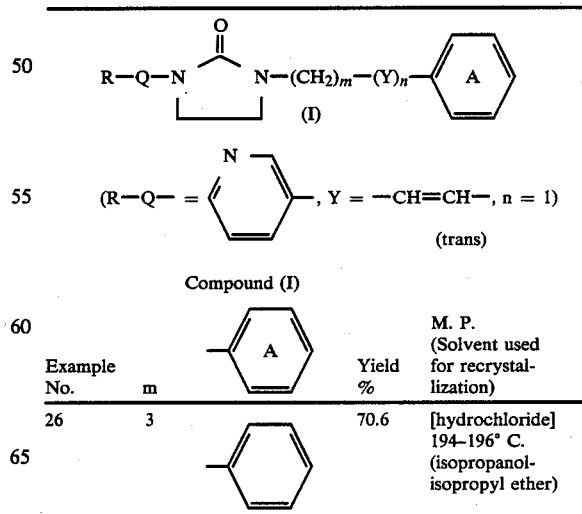

| Example No. | m | A | Yield % | M.P. (Solvent used for recrystallization) |
|---|---|---|---|---|
| 26 | 3 | phenyl | 70.6 | [hydrochloride] 194–196° C. (isopropanol-isopropyl ether) |

TABLE 1-3-continued

| No. | m | Ar | Yield % | M.P. (Solvent used for recrystallization) |
|---|---|---|---|---|
| 27 | 2 | 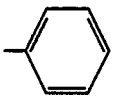 phenyl | 63.1 | [hydrochloride] 185–187° C. (isopropanol-isopropyl ether) |
| 28 | 6 |  phenyl | 83.6 | [hydrochloride] 162–164° C. (isopropanol-hexane) |
| 29 | 4 | 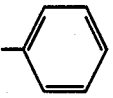 phenyl | 48.6 | [hydrochloride] 156–162° C. (isopropanol) |
| 30 | 5 | 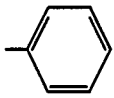 phenyl | 60.3 | [hydrochloride] 164–165° C. (isopropanol) |
| 31 | 3 | 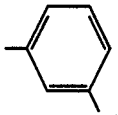 4-Cl-phenyl | 72.4 | [hydrochloride] 188–191° C. (ethanol) |
| 32 | 3 | 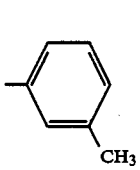 3-CH₃-phenyl | 75.1 | [hydrochloride] 181–185° C. (ethanol) |
| 33 | 3 | 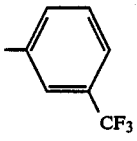 3-CF₃-phenyl | 60.1 | [hydrochloride] 167–170° C. (ethanol) |
| 34 | 3 | 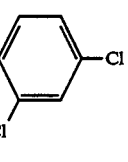 3,4-diCl-phenyl | 60.1 | [hydrochloride] 163–165° C. (ethanol) |
| 35 | 3 | 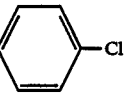 4-Cl-phenyl | 78.2 | 97–98° C. (ethyl acetate) |
| 36 | 3 | 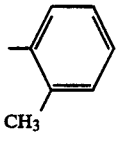 2-CH₃-phenyl | 51.3 | [hydrochloride] 178–179° C. (ethanol) |
| 37 | 3 | 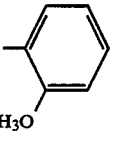 2-CH₃O-phenyl | 67.8 | [hydrochloride] 171–174° C. (acetone-ethanol-diethyl ether) |
| 38 | 3 | 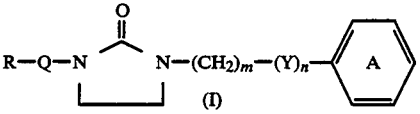 2-Cl-phenyl | 61.6 | [hydrochloride] 185–187° C. (ethanol) |

TABLE 1-4

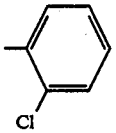

$$R-Q-N\overset{\overset{O}{\|}}{\underset{\underline{\hspace{1cm}}}{C}}N-(CH_2)_m-(Y)_n-A \quad (I)$$

(R—Q— = 4-pyridyl, ring A = phenyl, n = 0)

| Example No. | Compound (I) m | Yield % | M.P. (Solvent used for recrystallization) |
|---|---|---|---|
| 39 | 1 | 75.8 | [hydrochloride] 203–205° C. (ethanol-isopropyl ether) |
| 40 | 2 | 48.5 | 100–102° C. (isopropanol-isopropyl ether) |
| 41 | 3 | 82.3 | 69–70.5° C. (isopropanol-isopropyl ether) |

EXAMPLES 42 to 52

(1) By treating an aminopyridine compound (XI) and 2-chloroethylisocyanate compound (XII) in the same manner as in Example 1-(1), the compounds shown below in Table 2 were obtained.

TABLE 2

R—Q—NH₂ + X⁵CH₂CH₂NCO ⟶
(XI)      (XII)

(X⁵ = Cl)

R—Q—NHCONH—(CH₂)₂X⁵
(XIII)

| Example No. | Compound (XIII) R—Q— | M.P. (Solvent used for recrystallization) |
|---|---|---|
| 42-(1) | 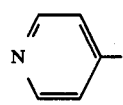 4-pyridyl | 114–117° C. (acetone) |
| 43-(1) |  2-pyridyl | 112.5–116° C. (acetone-isopropanol) |
| 44-(1) | 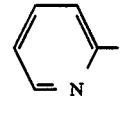 6-methyl-3-pyridyl | 130–132° C. (ethyl acetate-isopropyl ether) |

TABLE 2-continued

| | | |
|---|---|---|
| 45-(1) | CH3O-pyridyl | 130.5–132° C. (ethyl acetate-isopropyl ether) |
| 46-(1) | CH3O-pyridyl | 124–126° C. (benzene) |
| 47-(1) | CH3-pyridyl | 121–122° C. (ethyl acetate-isopropyl ether) |
| 48-(1) | thiazolyl | 153–154° C. (isopropanol) |
| 49-(1) | pyrimidyl | 164–167° C. (methanol) |
| 50-(1) | pyrazinyl | 147–150° C. (acetone) |
| 51-(1) | pyrimidyl | 147~150° C. (isopropanol) |
| 52-(1) | pyridyl-CH2- | 110~112° C. (isopropanol-isopropyl ether) |

(2) By treating the compounds obtained above in the same manner as in Example 1-(2), the compounds shown below in Table 3 were obtained.

TABLE 3

R—Q—NHCONH—(CH2)2X5 ⟶

(XIII)

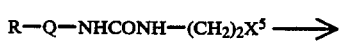

(III)

| Example No. | Compound (III) R—Q— | M. P. (Solvent used for recrystallization) |
|---|---|---|
| 42-(2) | 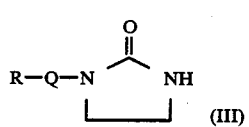 | 209~211° C. (isopropanol) |
| 43-(2) | pyridyl | 165~167° C. (ethanol) |
| 44-(2) | CH3-pyridyl | 200–202° C. (ethyl acetate-isopropyl ether) |
| 45-(2) | CH3O-pyridyl | 175–177° C. (ethyl acetate) |
| 46-(2) | CH3O-pyridyl | 157–161° C. (ethyl acetate) |
| 47-(2) | CH3-pyridyl | 192~194° C. (acetone-isopropyl ether) |
| 48-(2) | thiazolyl | 208~210° C. (ethanol) |
| 49-(2) | pyrimidyl | 269~275° C. (acetone - water) |
| 50-(2) | pyrazinyl | 188~191° C. (isopropanol) |
| 51-(2) | pyrimidyl | 228~230.5° C. (methanol) |
| 52-(2) | pyridyl-CH2- | 88~89° C. (ethyl acetate isopropyl ether) |

(3) By treating the imidazolidinone compound (III) obtained above and a cinnamyl compound (II) in the same manner as in Example 1-(3), the compounds shown below in Table 4 were obtained.

TABLE 4

 + 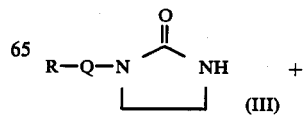

(III)

TABLE 4-continued $$X^1-(CH_2)_m-(Y)_n-\text{A} \quad \longrightarrow$$
(II)

($X^1$ = chlorine atom or p-toluenesulfonyl group)

R—Q—N—C(=O)—N—(CH$_2$)$_m$—(Y)$_n$—A
(I)

(ring A = phenyl, Y = —CH=CH— (trans), m and n = 1)

| Example No. | Compound (I) R—Q— | Yield % | M. P. (Solvent used for recrystallization) |
|---|---|---|---|
| 42-(3) | 4-pyridyl | 85.7 | 161~163° C. (isopropanol) |
| 43-(3) | 2-pyridyl | 77.9 | 91~92.5° C. (isopropyl ether) |
| 44-(3) | 4-methyl-2-pyridyl | 69.1 | 97~99° C. (isopropanol-isopropyl ether) |
| 45-(3) | 4-methoxy-3-pyridyl | 71.0 | 118~120° C. (ethyl acetate) |
| 46-(3) | 2-methoxy-4-pyridyl | 87 | 110~111° C. (ethyl acetate-hexane) |
| 47-(3) | 6-methyl-2-pyridyl | 75.6 | 103~104° C. (ethyl acetate-hexane) |
| 48-(3) | 2-thienyl | 66.6 | 103~105° C. (isopropanol-isopropyl ether) |
| 49-(3) | 2-pyrimidinyl | 58.0 | 118~120° C. (isopropanol-isopropyl ether) |
| 50-(3) | 4-pyrimidinyl | 87.7 | 134~135.5° C. (isopropanol) |
| 51-(3) | pyrazinyl | 64.3 | 129~131° C. (isopropanol) |
| 52-(3) | 2-pyridylmethyl | 60.0 | 64~67° C. (isopropanol-isopropyl ether) |

EXAMPLES 53 TO 95

By treating the imidazolidinone compounds (III) obtained in Examples 42-(2) to 52-(2) and a cynnamyl compound (II) in the same manner as in Example 1-(3), the compounds shown below in Tables 5-1 to 5-4 were obtained.

TABLES 5-1

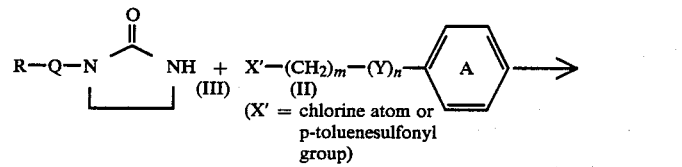

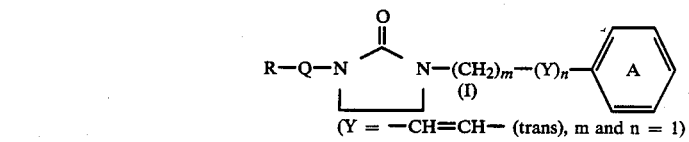

(Y = —CH=CH— (trans), m and n = 1)

| Example No. | R—Q— | A | Yield % | M. P. (Solvent used for recrystallization) |
|---|---|---|---|---|

TABLES 5-1-continued

| No. | Pyridyl | Aryl | Yield | m.p. (solvent) |
|---|---|---|---|---|
| 53 | 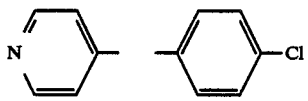 | 4-Cl-C₆H₄ | 61.0 | 187.5~190° C. (methanol-ethanol) |
| 54 | 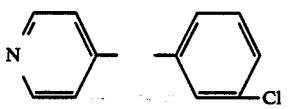 | 3-Cl-C₆H₄ | 60.1 | 122.5~124.5° C. (isopropanol) |
| 55 | 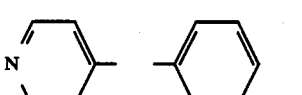 | 2-Cl-C₆H₄ | 65.4 | 179~182° C. (ethanol) |
| 56 | 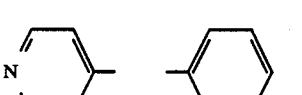 | 2-CH₃-C₆H₄ | 76.3 | 150~151.5° C. (isopropanol) |
| 57 | 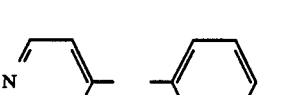 | 3-CH₃-C₆H₄ | 61.0 | 105~107° C. (isopropanol) |
| 58 | 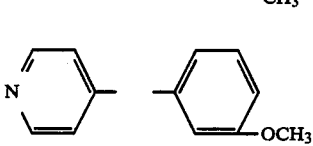 | 3-OCH₃-C₆H₄ | 67.3 | 132~134° C. (isopropanol) |
| 59 |  | 2-OCH₃-C₆H₄ | 61.3 | 154~157.5° C. (ethanol) |
| 60 | 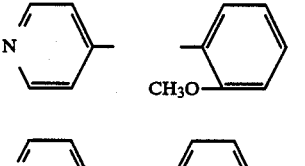 | 4-CH₃-C₆H₄ | 48.0 | 173~175° C. (isopropanol) |
| 61 | 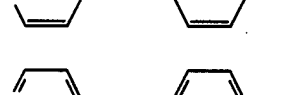 | 4-OCH₃-C₆H₄ | 72.9 | 143~145° C. (isopropanol) |
| 62 | 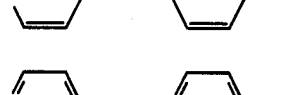 | 4-F-C₆H₄ | 69.3 | 151~152.5° C. (isopropanol) |
| 63 | 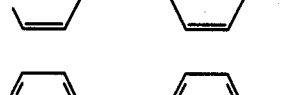 | 3-F-C₆H₄ | 66.1 | 152~154.5° C. (isopropanol) |
| 64 | 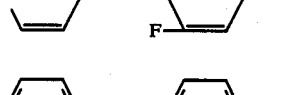 | 3,4-Cl₂-C₆H₃ | 58.1 | 151.5~153.5° C. (isopropanol) |
| 65 | 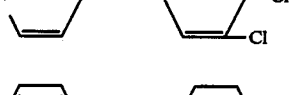 | 2-CF₃-C₆H₄ | 65.7 | 184~188° C. (isopropanol) |

TABLES 5-1-continued

| No. | Q (left structure) | A (right structure) | Yield % | M.P. (Solvent) |
|---|---|---|---|---|
| 66 | 4-pyridyl | phenyl-CF₃ (para) | 70.3 | 171~173° C. (isopropanol) |
| 67 | 4-pyridyl | phenyl-CF₃ (meta) | 69.3 | 141~142.5° C. (isopropanol) |
| 68 | 4-pyridyl | phenyl-NO₂ (para) | 41.3 | 187~189° C. (chloroform-ethyl acetate) |
| 69 | 4-pyridyl | phenyl-SCH₃ (meta) | 60.3 | 112~114° C. (isopropanol-isopropyl ether) |
| 70 | 4-pyridyl | phenyl-SCH₃ (para) | 60.0 | 161.5~163.5° C. (methanol) |
| 71 | 4-pyridyl | 2,3-dichlorophenyl | 71.0 | 175.5~177.5° C. (isopropanol) |
| 72 | 4-pyridyl | 2,4-dichlorophenyl | 45.3 | 161~163.5° C. (isopropanol) |
| 73 | 4-pyridyl | 2-(methylthio)phenyl | 63.0 | 157.5~160° C. (isopropanol) |
| 74 | 2-pyridyl | 2-chlorophenyl | 70.8 | 83~84.5° C. (isopropanol) |
| 75 | 2-pyrimidinyl | 2-chlorophenyl | 51.3 | 131~134° C. (isopropanol) |

TABLE 5-2

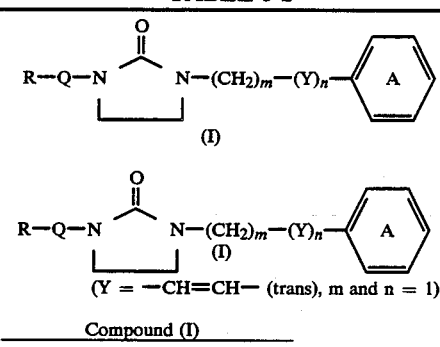

Compound (I)

$$R-Q-N\underset{\underset{O}{\|}}{\overset{}{\diagup}}N-(CH_2)_m-(Y)_n-A \quad (I)$$

$$R-Q-N\underset{\underset{O}{\|}}{\overset{}{\diagup}}N-(CH_2)_m-(Y)_n-A \quad (I)$$

(Y = —CH=CH— (trans), m and n = 1)

| Example No. | —(Y)ₙ— | A | Yield % | M.P. (Solvent used for recrystallization) |
|---|---|---|---|---|
| 76 | —CH=CH— (cis) | phenyl | 68.5 | 106~112° C. (isopropanol-isopropyl ether) |
| 77 | (—CH=CH—)₂ (trans) | phenyl | 61.5 | 175~176° C. (isopropanol) |

TABLE 5-2-continued

| 78 | (—CH=CH—)₂ (trans) | [3-Cl-phenyl] | 41.3 | 134~140° C. (chloroform isopropyl ether) |

TABLE 5-3

$$R-Q-N\underset{\underset{}{\big|\_\_\_\_\big|}}{\overset{O}{\|}}N-(CH_2)_m-(Y)_n-A \quad (I)$$

(R—Q=N⟨pyridyl⟩, Y = —CH=CH— (trans), n = 1)

| Example No. | m | Compound (I) A | Yield % | M. P. (Solvent used for recrystallization) |
|---|---|---|---|---|
| 79 | 3 | phenyl | 61.6 | 109~112° C. (isopropanol-isopropyl ether) |
| 80 | 2 | phenyl | 63.2 | 125~127° C. (isopropanol-isopropyl ether) |
| 81 | 5 | phenyl | 61.0 | 98~101° C. (chloroform-isopropyl ether) |
| 82 | 4 | phenyl | 64.2 | 105~107° C. (isopropyl ether) |
| 83 | 6 | phenyl | 81.0 | 97~99° C. (chloroform-hexane) |
| 84 | 3 | 4-Cl-phenyl | 60.7 | 61~62° C. (isopropanol-isopropyl ether) |
| 85 | 3 | 4-CH₃-phenyl | 57.0 | 80~82° C. (isopropanol-isopropyl ether) |
| 86 | 3 | 3-CH₃-phenyl | 63.4 | 99~100° C. (ethyl acetate) |
| 87 | 3 | 3-CF₃-phenyl | 65.3 | [hydrochloride] 177–180.5° C. (ethanol) |
| 88 | 3 | 2,4-diCl-phenyl | 62.0 | 81~83° C. (ethyl acetate-isopropyl ether) |
| 89 | 3 | 4-Cl-phenyl | 79.6 | 132~133° C. (ethyl acetate) |
| 90 | 3 | 3-CH₃O-phenyl | 63.1 | [hydrochloride] 166–168° C. (acetone-methanol) |
| 90 | 3 | 3-Cl-phenyl | 70.0 | 108.5–110.5° C. (isopropanol-isopropyl ether) |

TABLE 5-4

$$R-Q-N\underset{\underset{}{\big|\_\_\_\_\big|}}{\overset{O}{\|}}N-(CH_2)_m-(Y)_n-A \quad (I)$$

(ring A = phenyl, n = 0)

| Example No. | Compound (I) R—Q— | m | Yield (%) | M.P. (Solvent used for recrystallization) |
|---|---|---|---|---|
| 92 | 4-pyridyl | 1 | 65.3 | [hydrochloride] 255–258° C. (ethanol-isopropyl ether) |
| 93 | 4-pyridyl | 2 | 48.2 | 108–109° C. (isopropanol-isopropyl ether) |
| 94 | 2-pyridyl | 1 | 53.8 | [hydrochloride] 149–151° C. (isopropanol-isopropyl ether) |
| 95 | 2-pyridyl | 2 | 62.4 | [hydrochloride] 53–56° C. (ethanol-isopropyl ether) |

EXAMPLE 96

(1) To a solution of 1.6 g of N-(3-pyridylmethyl)-ethylenediamine dissolved in 30 ml of tetrahydrofuran, 1.49 g of carbonyldiimidazole was added at 0° C. The mixture was stirred at 0° C. for 30 minutes, then at room temperature for 4 hours. The solvent was distilled off, and the residue was purified by silica gel column chromatorgraphy (solvent: chloroform-methanol=15:1) and recrystallized from a mixture of isopropanol and hexane to give 1.43 g of 1-(3-pyridyl-methyl)-2-imidazolidinone.

M.P.: 58°-86° C.

(2) By treating 1-(3-pyridylmethyl)-2-imidazolodinone obtained above and cinnamyl chloride (trans-form) in the same manner as in Example 1-(3), (E)-1-cinnamyl-3-(3-pyridylmethyl)-2-imidazolidinone was obtained.

Yield: 65.0%.

M.P.: (oxalate) 105°-115° C. (decompd) (recrystallized from isopropanol-isopropyl ether).

EXAMPLE 97

(1) By treating N-(4-pyridylmethyl)-ethylenediamine in the same manner as in Example 96-(1), 1-(4-pyridyl-methyl)-2-imidazolidinone was obtained.

M.P.: 153°-155° C. (recrystallized from isopropanol-isopropyl ether).

(2) By treating 1-(4-pyridylmethyl)-2-imidazolidinone and cinnamyl chloride (trans-form) in the same manner as in Example 1-(3), (E)-1-cinnamyl-3-(4-pyridylmethyl)-2-imidazolidinone was obtained.

Yield: 69.8%.

M.P.: (hydrochloride) 150°-152° C. (recrystallized from isopropanol-isopropyl ether).

EXAMPLE 98

To a solution of 20 g of N-(2-chloroethyl)-N'-(3-pyridyl) urea dissolved in 200 ml of dimethyl sulfoxide, 13 g of KOH powder was added under ice-cooling, and the mixture was stirred at room temperature for 1.5 hours. Further, 3.4 g of KOH powder was added and then 16.8 g of cinnamyl chloride (trans-form) was added under ice-cooling and the mixture was stirred for 20 minutes, followed by stirring at room temperature for 30 minutes. The mixture was diluted with 300 ml of water, and extracted with ethyl acetate. The ethyl acetate layer was washed with water, saturated saline water ad dried, and ethyl acetate was distilled off. To the residue was added 100 ml of 70% acetic acid, and the mixture was heated at 90° C. for 10 minutes and then concentrated under reduced pressure. The residue was dissolved in ethyl acetate and washed twice with saturated saline water and twice with water, and dried. After distilling the ethyl acetate off, the residue was recrystallized from ethanol to give 21.96 g of (E)-1-cinnamyl-3-(3-pyridyl)-2-imidazolidinone.

Yield: 78.6%.

The physico-chemical properties of this product were identical with those of the sample obtained in Example 1.

EXAMPLES 99 TO 105

(1) By treating an amine compound (XI) and 2-chloro-ethylisocyanate (XII) in the same manner as in Example 1-(1), the compounds shown below in Table 6 were obtained.

TABLE 6

R—Q—NH$_2$ + X$^5$(CH$_2$)$_2$NCO ——→

(XI)       (XII)

TABLE 6-continued

R—Q—NHCONH—(CH$_2$)$_2$X$^5$ (XIII)

(X$^5$ = Cl)

| Example No. | Compound (XIII) R—Q— | M.P. (Solvent used for recrystallization) |
|---|---|---|
| 99-(1) | CH$_3$-pyridyl | 126~127° C. (acetone) |
| 100-(1) | pyridyl-CH$_3$ | 135~137° C. (acetone) |
| 101-(1) | CH$_3$-pyridyl-CH$_3$ | 139~141° C. (acetone) |
| 102-(1) | Cl-pyridyl | 165~166° C. (acetone) |
| 103-(1) | pyridazinyl (N=N) | 169~171° C. (methanol) |
| 104-(1) | pyridazinyl | 163~164° C. (methanol) |
| 105-(1) | pyrimidinyl | 154~156° C. (isopropanol-isopropyl ether) |

(2) By treating the compounds obtained above in the same manner as in Example 98, the compounds shown in Table 7 were obtained.

TABLE 7

R—Q—NHCONH—(CH$_2$)$_2$X$^5$ ——→

(XIII)

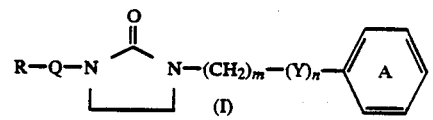

(ring A = phenyl, Y = —CH=CH— (trans), m and n = 1)

| Example | Compound (I) | Yield | M.P. (Solvent used for |

TABLE 7-continued

| No. | R—Q— | (%) | recrystalization) |
|---|---|---|---|
| 99-(2) | (2-methyl-pyridinyl structure, CH3 on position) | 62.0 | 107~108° C. (ethyl acetate) |
| 100-(2) | (methyl-pyridinyl structure, CH3 other position) | 61.3 | [oxalate] 82-85° C. (isopropanol) |
| 101-(2) | (CH3-pyridinyl structure) | 68.0 | [hydrochloride. MeOH] 114-115° C. (methanol-ethyl acetate) |
| 102-(2) | (Cl-pyridinyl structure) | 76 | 117~118° C. (ethyl acetate) |
| 103-(2) | (pyridazinyl N—N structure) | 89 | 117~118° C. (chloroform-ethanol) |
| 104-(2) | (pyrimidinyl structure) | 62 | 188~190° C. (isopropanol) |
| 105-(2) | (pyrazinyl structure) | 80 | 107~109° C. (isopropanol-isopropyl ether) |

EXAMPLE 106

(1) A solution of 11 g of N-(4-pyridyl)ethylenediamine and 5.3 g of 2-nitrocinnamyl chloride (trans-form) dissolved in 60 ml of ethanol was stirred at room temperature for 30 minutes and then stirred at 50° C. for 90 minutes. The solvent was distilled off under reduced pressure, and 10% aqueous sodium hydroxide was added to the residue and the mixture was extracted with chloroform. After drying of the extract, chloroform was distilled off and the residue was purified by silica gel column chromatography (solvent: chloroform-methanol-triethylamine=20:1:0.1) to give 2.33 g of (E)-N-(2-nitrocinnamyl)-N'-(4-pyridyl)ethyenediamine as a yellow oily substance.

MS (m/e): 298 (M+).

(2) To a solution of 2.33 g of (E)-N-(2-nitrocinnamyl)-N'-(4-pyridyl)ethylenediamine dissovled in a mixture of 50 ml of tetrahydrofuran and 50 ml of chloroform was added 1.52 g of carbonyldiimidazole at 0° C. The mixture was stirred at room temperature for 40 hours. The solvent was distilled off under reduced pressure, and the residue was extracted with chloroform. The chloroform layer was washed with water, dried and the solvent was distilled off. The residue was purified by silica gel column chromatography (solvent: chloroform-methanol=3:1) and recrystallized from a mixture of isopropanol and methanol to give 1.44 g of (E)-1-(2-nitrocinnamyl)-3-(4-pyridyl)-2-imidazolidinone.

Yield: 56.8%.
M.P.: 205°-206° C. (decompd.).

EXAMPLE 107

(1) By treating 10 g of N-(3-pyridyl)ethylenediamine and 4.5 g of cinnamyl chloride (trans-form) in the same manner as in Example 106-(1), 2.91 g of (E)-N-cinnamyl-N'-(3-pyridyl)ethylenediamine was obtained as an oily substance.

MS (m/e): 253 (M+).

(2) By treating 2.53 g of (E)-N-cinnamyl-N'-(3-pyridyl)ethylenediamine and 1.63 g of carbonyldiimidazole in the same manner as in Example 106-(2), 1.96 g of (E)-1-cinnamyl-3-(3-pyridyl)-2-imidazolidinone was obtained.

Yield: 70%.

The physico-chemical properties of this product were identical with those of the sample obtained in Example 1.

EXAMPLE 108

(1) To a solution of 5.37 g of (E)-N-cinnamyl-N'-(3-pyridyl)ethylenediamine dissolved in 100 ml of tetrahydrofuran, 4.5 g of triethylamine was added and the mixture was ice-cooled. To the mixture was added dropwise 20 ml of a tetrahydrofuran solution containing 5.12 g of thiophosgene over 5 minutes, and subsequently the mixture was stirred under ice-cooling for 30 minutes and then at room temperature for 2 hours. The solvent was distilled off, and the residue was dissolved in chloroform, washed with water and dried, followed by distillation of the solvent. The residue was purified by silica gel column chromatorgraphy (solvent: chloroform-methanol=20:1) to give 2.86 g of (E)-1-cinnamyl-3-(3-pyridyl)imidazolidine-2-thione as caramel.

MS (m/e: 295 (M+).

(2) To a solution of 3.02 g of (E)-1-cinnamyl-3-(3-pyridyl)imidazolidine-2-thione dissolved in 40 ml of 4N hydrochloric acid, 10 ml of an aqueous solution of 1.03 g of NaNO2 was added dropwise. After stirring at room temperature for 1 hour, the mixture was made alkaline by addition of a sodium hydroxide solution, and the precipitated crystals were collected by filtration. The crystals obtained were washed with water, dried and then purified by silica gel column chromatorgraphy (solvent: chloroform-methanol=30:1), followed by recrystallization from ethanol, to give 1.74 g of (E)-1-cinnamyl-3-(3-pyridyl)-2-imidazolidinone.

Yield: 61%.

The physico-chemical properties of this product were identical with those of the sample obtained in Example 1.

EXAMPLE 109

(1) To 50 ml of a tetrahydrofuran solution containing 16.2 g of carbonyldiimidazole, a solution of 9.4 g of 3-aminopyridine dissolved in 50 ml of tetrahydrofuran was added dropwise under ice-cooling over 5 minutes. After stirring under ice-cooling for 30 minutes and at room temperature for 1 hour, the mixture was again ice-cooled, and 1.33 g of (E)-cinnamylamine was added, followed by stirring at room temperature for 18 hours. After distilling the solvent off, the residue was dissolved in ethyl acetate, washed with water and dried, followed by distillation of the solvent. The residue was purified by silica gel column chromatography (solvent: chloroform-methanol=20:1) to give 5.9 g of (E)-N-cinnamyl-N'-(3-pyridyl) urea as colorless caramel.

MS (m/e): 253 (M+).

(2) To a solution of 2.51 g of (E)-N-cinnamyl-N'-(3-pyridyl) urea dissolved in 30 ml of dimethylformamide, 990 mg of sodium hydride (60% oily dispersion) was added under ice-cooling and the mixture was stirred for 30 minutes. To the mixture was added 2.8 g of 1-chloro-2-p-toluenesulfonyloxyethane and the mixture was stirred under ice-cooling for 6 hours. After distilling dimethylformamide off under reduced pressure, the residue was diluted with water and extracted with chloroform. The chloroform layer was washed with water, dried and then the solvent was distilled off. The residue was purified by silica gel column chromatography (solvent: chloroform-methanol=30:1) and recrystalliezed from ethanol to give 1.65 g of (E)-1-cinnamyl-3-(3-pyridyl)-2-imidazolidinone.

Yield: 60%.

The physico-chemical properties of this product were identical with those of the sample obtained in Example 1.

EXAMPLE 110

(1) To a solution of 100 g of methyl crotonate dissolved in 340 ml of carbon tetrachloride, 178 g of N-bromo-succinimide and 800 mg of benzoyl peroxide were added, and the mixture was heated under reflux for 4 hours. After cooling to room temperature, insolubles were filtered off, and the mother liquor was purified by distillation under reduced pressure to give 111 g of methyl 4-bromocrotonate as an oily substance.

B.P.: 85°-92° C./13 mmHg.

(2) A mixture of 11 g of methyl 4-bromocrotonate and 103 g of triethyl phosphage was introduced into a flask heated to 120° C. filled with argon gas stream over 30 minutes. After the mixture was heated under reflux of 4 hours, the product was purified by distillation under reduced pressure to give 123 g of methyl 4-diethyl-phosphonocrotonate as an oily substance.

B.P.: 120°-125° C./0.4 mm Hg.

(3) To a solution of 500 mg of o-chlorobenzaldehyde and 840 mg of methyl 4-diethylphosphonocrotonate dissolved in 5 ml of tetrahydrofuran, 142 mg of sodium hydride (60% oily dispersion) was added under ice-cooling. Imeediately, 2 ml of dimethylformamide was added and the mixture was stirred at room temperature for 2 hours. The mixture was poured into water and extracted twice with ether. The organic layer was washed twice with water, dried and the solvent was removed by distillation. The residue was purified by silica gel column chromatography (solvent: hexane-ethyl acetate=20:1) to give 650 mg of methyl (2E, 4E)-5-(2-chlorophenyl)-2,4-pentadienoate as an oily substance.

(4) To a solution of 20 g of methyl (2E, 4E)-5-(2-chlorophenyl)-2,4-pentadienoate dissolved in 150 ml of toluene, 215 ml of diisobutylaluminum hydride (1.5M toluene solution) was added dropwise under ice-cooling over 1 hour. After stirring at the same temperature for 5 minutes, saturated aqueous ammonium chloride was slowly added, and the insolubles were filtered off. The filtrate was washed twice with saturated aqueous ammonium chloride, dried and then the solvent was distilled off to give 16.4 g of (2E, 4E)-5-(2-chlorophenyl)-2,4-pentadien-1-ol as an oily substance.

(5) To a solution of 1.43 g of (2E, 4E)-5-(2-chlorophenyl)-2,4-pentadien-1-ol dissolved in 10 ml of tetrahydrofuran, 4.83 ml of n-butyl lithium (1.6M hexane solution) was added under cooling to −70° C. After stirring for 5 minutes, a solution of 1.4 g of p-toluenesulfonyl chloride dissolved in 5 ml of tetrahydrofuran was promptly added dropwise, and the temperature was elevated to room temperature within 10 minutes (this solution is referred to as Solution A).

On the other hand, 1.08 g of N-(3-pyridyl)-2-imidazolidinone was dissolved in 10 ml of dimethylformamide and 265 mg of sodium hydride (60% oily dispersion) was added at room temperature thereto. After stirring at the same temperature for 10 minutes, the reaction mixture was added to the Solution A obtained above at −70° C., and the mixture was stirred at the same temperature for 10 minutes and at room temperature for 2 hours. The reaction mixture was poured into water, extracted with ethyl acetate, washed three times with water, dried and then the solvent was distilled off. The residue was purified by silica gel column chromatography (solvent: chloroform:acetone=2:1) and recrystallized from methanol to give 1.1 g of (2E, 4E)-1-(5-(2-chlorophenyl)-2,4-pentadienyl)-3-(3-pyridyl)-2-imidazolidinone as needles.

M.P.: 130°-133° C.

REFERENTIAL EXAMPLE 1

(1) To a solution of 11.2 g of phenylacetylene dissolved in 100 ml of tetrahydrofuran, 78.8 ml of 1.6M-hexane solution of n-butyl lithium was added dropwise at 5°-8° C. Then 150 ml of a hexamethylphosphoramide solution containing 29.4 g of 1-bromo-6-(2-tetrahydropyranyloxy)-hexane was added dropwise at 10°-20° C. After stirring at 20° C. for 30 minutes, the reaction mixture was poured into ice-water and extracted with hexane. The organic layer was washed with water, dried and then the organic solvent was distilled off. The residue was purified by silica gel column chromatography (solvent: hexane-ethyl acetate=10:1), to give 18.3 g of 1-phenyl-8-(2-tetrahydropyranyloxy)-1-octyne as an oily substance.

MS (m/e): 286 (M+).

This product and the products obtained in the following Referential examples were used as such without isolation or purification in the subsequent steps or as the starting materials for Examples.

(2) To 150 ml of a mixture of tetrahydrofuran-diglyme (2:15) were added 12 g of 1-phenyl-8-(2-tetrahydropyranyloxy)-1-octyne and 3.35 g of lithium aluminum hydride. The mixture was heated and tetrahydrofuran was distilled off until the inner temperature became 120° C. After heating under reflux at the same temperature for 1 hour, the mixture was ice-cooled. Ice was added to the mixture and the mixture was extracted with ethyl acetate. The organic layer was washed with 10% hydrochloric acid, water, sodium hydrogen carbonate solution, saline water in the order mentioned, dried, and then the solvent was distilled off. The residue was dissolved in 250 ml of methanol and 1.1 g of p-toluenesulfonic acid was added thereto. The mixture was stirred at room temperature for 1 hour and 2 ml of triethylamine was added to the mixture. Methanol was distilled off and the residue was purified by silica gel column chromatorgraphy (solvent: hexane-ethyl acetate=3:1) to give 7.5 g of (E)-8-phenyl-7-octen-1-ol as an oily substance.

Yield: 87.6%.

MS (m/e): 186 (M—H₂O) 204 (M+).

(3) To a solution of 7.5 g of (E)-8-phenyl-7-octen-1-ol dissolved in 60 ml of pyridine, 9.1 g of p-toluenesulfonyl chloride was added at 0° C. After stirring at 10° C. for 5 hours, 10 ml of water was added and the mixture was stirred for 30 minutes, followed by addition of 200 ml of ether. The mixture was washed with 10% aqueous hydrochloric acid, water and saturated saline water. The organic layer was dried, and the solvent was removed under reduced pressure. The pale yellow oily product obtained was purified by silica gel column chromatography (solvent: hexane-ethyl acetate=5:1) to give 12 g of (E)-1-phenyl-8-p-toluenesulfonyloxy-2-octene as an oily product.

MS (m/e): 358 (M+), 186 (M—TsOH).

REFERENTIAL EXAMPLES 2 AND 3

(1) Phenylacetylene and a tetrahydropyranyloxy compound were treated in the same manner as in Referential example 1-(1) to give the compounds shown below in Table 8.

TABLE 8

$$\text{A}-C\equiv CH + Br-(CH_2)_m-O\text{(THP)} \longrightarrow$$

$$\text{A}-C\equiv C-(CH_2)_m-O\text{(THP)}$$

(VII)

| Referential Example No. | Compound (VIII) A = | m | Physical Property |
|---|---|---|---|
| 2-(1) | phenyl | 4 | Oily substance |
| 3-(1) | phenyl | 5 | Oily substance |

(2) The compounds obtained above were treated in the same manner as in Referential example 1-(2) to give the compounds shown below in Table 9.

TABLE 9

$$\text{A}-C\equiv C(CH_2)_m-O\text{(THP)} \longrightarrow$$

(VIII)

$$\text{A}-(Y)_n-(CH_2)_m-OH$$

(IX)

(Y = —CH=CH—(trans), n = 1)

| Referential Example No. | Compound (IX) A = | m | Physical Property |
|---|---|---|---|
| 2-(2) | phenyl | 4 | Oily substance |
| 2-(2) | phenyl | 5 | Oily substance |

(3) The compounds obtained above were treated in the same manner as in Referential example 1-(3) to give the compounds shown below in Table 10.

TABLE 10

$$\text{A}-(Y)_n-(CH_2)_m-OH \longrightarrow$$

(IX)

$$\text{A}-(Y)_n-(CH_2)_m-X^1$$

(II)

(Y = —CH=CH—(trans), n = 1, $X^1$ = toluenesulfonyloxy group)

| Referential Example No. | Compound (II) A = | m | Physical Property |
|---|---|---|---|
| 2-(3) | phenyl | 4 | Oily substance |
| 3-(3) | phenyl | 5 | Oily substance |

REFERENTIAL EXAMPLE 4

(1) To a suspension of 4 g of benzyltriphenylphosphonium chloride in 20 ml of tetrahydrofuran was added 7.07 ml of 1.6M hexane solution of n-butyl lithium under cooling at 0° C. After stirring at room temperature for 30 minutes, 1 g of 2-hydroxytetrahydrofuran was added, followed by stirring at room temperature for 16 hours. Subsequently, after refluxing for 2 hours, insolubles were filtered off and the solvent was distilled off. The residue was purified by silica gel column chromatography (solvent: hexane-ethyl acetate=2:1) to give 2 g of (E)-5-phenyl-4-penten-1-ol as a colorless oily substance.

MS (m/e): 162 (M+), 144 (M—H₂O).

(2) By treating the compound obtained above in the same manner as in Referential example 1-(3), (E)-1-phenyl-5-(p-toluenesulfonyloxy)-1-pentene was obtained as an oily substance.

REFERENTIAL EXAMPLES 5 TO 12

(1) A triphenylphosphonium compound was treated in the same manner as in Referential example 4-(1) to give the compounds shown below in Table 11.

TABLE 11

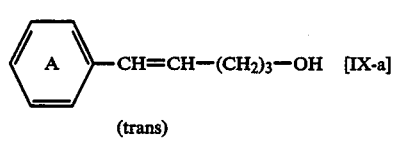

Compound [IX-a]

| Referential Example No. | A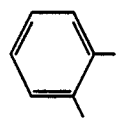 | Physical Property |
|---|---|---|
| 5-(1) | 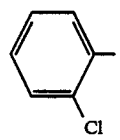 Cl (ortho) | Oily substance |
| 6-(1) | 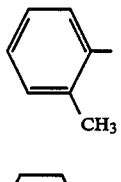 CH₃ (ortho) | Oily substance |
| 7-(1) | 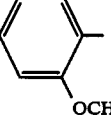 OCH₃ (ortho) | Oily substance |
| 8-(1) | 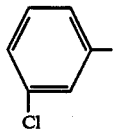 Cl (meta) | Oily substance |
| 9-(1) | 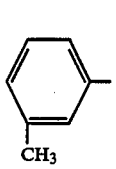 CH₃ (meta) | Oily substance |
| 10-(1) | 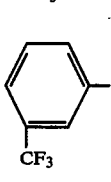 CF₃ (meta) | Oily substance |

TABLE 11-continued

| 11-(1) | 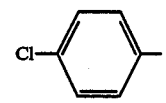 Cl—phenyl | Oily substance |
| 12-(1) | 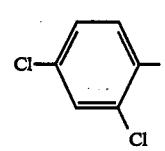 Cl, Cl disubstituted | Oily substance |

(2) The compounds obtained above were treated in the same manner as in Referential example 1-(3) to give the compounds shown below in Table 12.

TABLE 12

[IX-a] → A—CH=CH—(CH₂)₃—X¹
(trans)  [II-a]

(X¹ = p-toluenesulfonyloxy group)

Compound [II-a]

| Referential Example No. | A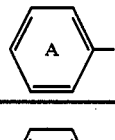 | Physical Property |
|---|---|---|
| 5-(2) | 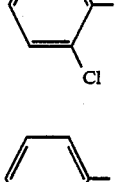 Cl (ortho) | Oily substance |
| 6-(2) | 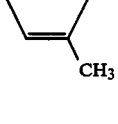 CH₃ (ortho) | Oily substance |
| 7-(2) | 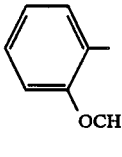 OCH₃ (ortho) | Oily substance |
| 8-(2) | 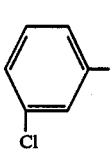 Cl (meta) | Oily substance |
| 9-(2) | 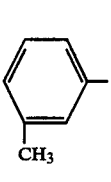 CH₃ (meta) | Oily substance |

TABLE 12-continued

| | | |
|---|---|---|
| 10-(2) | [phenyl with CF3 substituent] | Oily substance |
| 11-(2) | [Cl-phenyl] | Oily substance |
| 12-(2) | [dichlorophenyl with 2 Cl] | Oily substance |

What is claimed is:

1. An imidazolidinone compound of the formula:

$$R-Q-N\underset{\underline{\quad\quad}}{\overset{O}{\overset{\|}{C}}}N-(CH_2)_m-(Y)_n-A \quad (I)$$

wherein

Q is methylene group or a single bond:

R is a heterocyclic group selected from the group consisting of pyridyl, pyridazinyl, pyrimidinyl, pyrazinyl and 1,3-thiazolyl which may be unsubstituted or substituted with a substituent selected from the group consisting of lower alkyl, a lower alkoxy and halogen atom and wherein R is bonded to Q or, when Q is a single bond, to the imidazolidinone ring, through the carbon atom of R;

the ring A is an unsubstituted phenyl group or a phenyl group having 1 or 2 substituent(s) selected from the group consisting of lower alkyl, lower alkoxy, halogen, lower alkylthio, trihalogeno-lower alkyl and nitro;

Y is vinylene group or ethynylene;

m is an integer from 1 to 6 and n is 0, 1 or 2, or a pharamacutically acceptable salt thereof.

2. The compound according to claim 1, in which R is an unsubstituted pyridyl or a pyridyl group having a substituent selected from the group consisting of lower alkyl, lower alkoxy and halogen; pyridazinyl; pyrimidinyl; pyrazinyl; or 1,3-thiazolyl; or a pharmaceutically acceptable salt thereof.

3. The compound according to claim 2, in which Y is vinylene.

4. The compound according to claim 3, in which R is pyridyl, lower alkyl-pyridyl or pyrimidinyl, or a pharamceutically acceptable salt thereof.

5. The compound according to claim 4, in which Q is a single bond;

R is pyridyl, methylpyridyl or pyrimidinyl and wherein R is bonded to the imidazolidinone ring through the carbon atom of R;

the ring A is an unsubstituted phenyl or a phenyl having a substituent selected from the group consisting of lower alkyl, lower alkoxy, halogen and trihalogenomethyl;

m is an integer from 1 to 3 and n is 1, or a pharmaceutically acceptable salt thereof.

6. The compound according to claim 5, in which ring A is phenyl, methylphenyl, methoxyphenyl, chlorophenyl or trifluoromethylphenyl, or a pharmaceutically acceptable salt thereof.

7. The compound according to claim 6, in which R is 3-pyridyl, 4-pyridyl, 6-methyl-2-pyridyl or 2-pyrimidinyl and ring A is phenyl, 2-methylphenyl, 3-methylphenyl, 2-methoxyphenyl, 3-methoxyphenyl, 2-chlorophenyl, 3-chlorphenyl, 4-chlorophenyl, 2-trifluoromethylphenyl or 3-trifluoromethylphenyl, or a pharmaceutically acceptable salt thereof.

8. The compound according to claim 7, in which the ring A is phenyl, 3-methylphenyl, 2-chlorophenyl, 3-chlorophenyl or 4-chlorophenyl and m is 1 or 3, or a pharmaceutically acceptable salt thereof.

9. The compound according to claim 8, which is 1-cinnamyl-3-(3-pyridyl)-2-imidazolidinone, or a pharmaceutically acceptable salt thereof.

10. The compound according to claim 8, which is (E)-1-cinnamyl-3-(3-pyridyl)-2-imidazolidinone, or a pharmaceutically acceptable salt thereof.

11. The compound according to claim 8, which is 1-cinnamyl-3-(6-methyl-2-pyridyl)-2-imidazolidione, or a pharmaceutically acceptable salt thereof.

12. The compound according to claim 8, which is (E)-1-cinnamyl-3-(6-methyl-2-pyridyl)-2-imidazolidinone, or a pharmaceutically acceptable salt thereof.

13. A pharmaceutical composition possessing an activating effect on cerebral metabolism, or nootropic or antidepressive effect which comprises as an active ingredient a therapeutically effective amount of the compound according to claims 1, 5, 8, 10 or 12 or a pharmaceutically acceptable salt thereof in association with a pharmaceutically acceptable carrier therefor.

14. A method of producing an activating effect on cerebral metabolism in a warm-blooded animal comprising administering to said warm-blooded animal a cerebral activating amount of the compound according to claims 1, 5, 8, 10 or 12 or a pharmaceutically acceptable salt thereof.

15. A method of producing a nootropic effect in a warm-blooded animal comprising administering to said warm-blooded animal a nootropic effective amount of the compound according to claims 1, 5, 8, 10 or 12 or a pharmaceutically acceptable salt thereof.

16. A method of producing an antidepressive effect in a warm-blooded animal comprising administering to said warm-blooded animal an anti-depressive effective amount of the compound according to claims 1, 5, 8, 10 or 12 or a pharmaceutically acceptable salt thereof.

* * * * *